United States Patent [19]

Bordini

[11] Patent Number: 4,847,487
[45] Date of Patent: Jul. 11, 1989

[54] DEVICE FOR DETECTING THE PRESENCE OF PRODUCTS IN RELATED SEATS AND ANY IRREGULARITY IN THE BASE SECTION OF THESE PRODUCTS WHEN ALREADY LOCATED IN THEIR RELATED SEATS

[75] Inventor: Fausto Bordini, Bubano, Italy

[73] Assignee: I.M.A. Industria Macchine Automatiche S.p.A., Ozzano Dell'Emilia, Italy

[21] Appl. No.: 126,595

[22] Filed: Nov. 30, 1987

[30] Foreign Application Priority Data

Dec. 23, 1986 [IT] Italy ................. 3620 A/86

[51] Int. Cl.⁴ ............................................. G01N 9/04
[52] U.S. Cl. .............................................. 250/223 R
[58] Field of Search ............. 250/223 R, 223 B, 571, 250/572, 222.2, 222.1; 53/53, 54, 499, 500; 209/536

[56] References Cited

U.S. PATENT DOCUMENTS

| | | |
|---|---|---|
| 3,980,180 | 9/1976 | Jamieson .................... 250/223 R |
| 4,245,243 | 1/1981 | Gutjahr et al. ............. 250/223 R |
| 4,384,303 | 5/1983 | Brenke et al. ............. 250/223 R |
| 4,399,367 | 8/1983 | Grube et al. .............. 250/223 R |
| 4,472,922 | 9/1984 | Romagnoli ........................ 53/53 |

Primary Examiner—David C. Nelms
Assistant Examiner—Michael Messinger
Attorney, Agent, or Firm—Darby & Darby

[57] ABSTRACT

A device and method for detecting the presence of products in related seats and any irregularities in the base section of the products. The device includes a row of radiation emitters and a row of receivers. A belt with transverse rows of seats each containing products is moved between the emitters and receivers. The receivers detect any radiation which passes through the seats unshadowed by the products. Since the base section of whole and unbroken products should completely shadow the receivers, any break or missing portion of the base section is detected when radiation reaches the receiver. Cone-shaped conveyors are provided to convey radiation to the receivers so as to reduce the required size of the receivers.

16 Claims, 2 Drawing Sheets

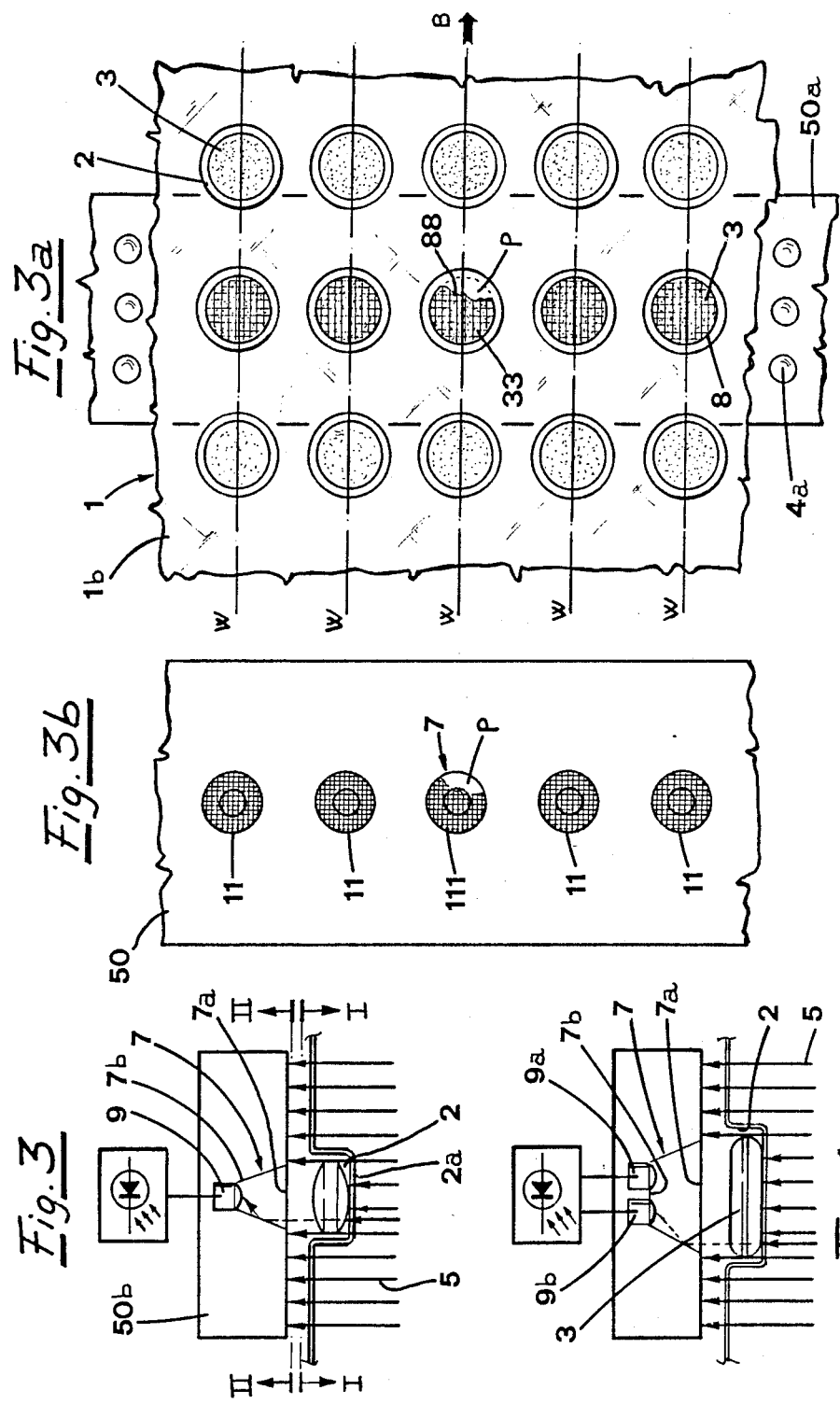

DEVICE FOR DETECTING THE PRESENCE OF PRODUCTS IN RELATED SEATS AND ANY IRREGULARITY IN THE BASE SECTION OF THESE PRODUCTS WHEN ALREADY LOCATED IN THEIR RELATED SEATS

BACKGROUND OF THE INVENTION

The present invention concerns devices that are required to perform a dual function, namely that of checking the presence of products in corresponding cells, as well as that of checking the base section of these products, this base section being evaluated in a preset direction.

DESCRIPTION OF THE PRIOR ART

A technical sector in which these machines are used to great advantage is very specifically that involved in the packaging of products (e.g.: pharmaceuticals, sweets, etc) using what are known as "blister packs".

In this sector a belt of synthetic resin (suitable for heat-molding) is made to move (intermittently or continuously) by a motor, and is subjected, in intermittent cycles, to a heat-molding stage in which consecutive strips of the belt are made to form the same number of groups of cells (seats), the latter being laid out in longitudinal and transverse rows, that are respectively parallel and perpendicular to the axis of the belt.

Downstream of the heat molding station, there is a station for filling the cells, in which suitable means load the products into the cells. (e.g: one product for each cell).

Downstream of this station, in relation to the direction of movement of the belt, there is a sealing station in which suitable means apply metal foil, by means of heat welding, to the face of the belt into which the cells open.

Once the belt has been sealed in this way, it moves on to a subsequent station in which cutting means with intermittent operation form a corresponding blister pack for every stroke in their operating cycle.

To optimize packaging, there must be a check for any blister packs in which one of the related cells has not been filled with product, or where, if filled, the product is not whole (e.g. is in fragments, or lacks certain parts in comparison with the ideal product shape). Any such blister packs must be rejected before being sent to a packaging station where one or more blister packs are inserted in a related box.

Excepting for those cases in which the removal of faulty blister packs is effected manually following a visual check on their contents by the operator, it is effected by suitable means operated by a product check and reject control unit, receiving information from a device located between the said filling and sealing stations, and able to detect whether a product is missing from its related cell; more sophisticated versions also being able to detect whether any parts of the product are missing, evaluating the base section of the product in a direction perpendicular to the belt.

In its most widely used form, this device is composed of a pair of detection means located in a transverse plane that is perpendicular to the belt, each of which comprises a device for emitting electromagnetic radiation (e.g.: infra-red rays), located opposite one side of the belt, and a device for receiving the said radiation, located opposite the other side of the belt; the said emitter and receiver are aligned in a direction perpendicular to the belt, and are positioned in the longitudinal plane along which a corresponding longitudinal row of cells passes.

The band of radiation is partially absorbed by the belt, and this is taken into account when calibrating the transmitter-receiver pair; this absorption is obviously increased when the product is present in the cell.

As a result of this, the electronic output signal of the receiver has two significantly different values depending upon whether the product is present in the cell or not.

The aforementioned unit only processes the signal coming from the receiver when a cell is coaxial to the said emitter-receiver, this depending upon the speed with which the cells in a longitudinal row move between the emitter and receiver.

The inspection (or detection) is effected on a single part of the cell (in some cases more than one) such that the only information supplied is whether the product is or is not present in the cell.

The above solution does not thus enable one to detect whether any parts of the product are missing, or whether it is present in fragments alone. The limitations of such a solution are obvious.

A more sophisticated form of the device uses a telecamera which examines the base section of the product in a direction perpendicular to the bottom of the cell.

The device needs to be set up in advance in order to be able to perform this function, it being necessary to analyze the base section of a product that is whole and perfectly intact. The base section is divided into a grid of parallel segments, each segment being delineated by the outline of the aforesaid base section; each segment is "measured" using an infinitesimal unit of length so that the total of these segment "measurements" is proportional to the area of the base section.

This solution is capable of performing the dual function mentioned in the introduction, namely that of detecting the presence of the product in its related cell, at the same time checking for any irregularities in the above-mentioned base section (e.g. parts of the product missing, the product being present in fragments).

The complexity of this solution, together with its consequently high production and running costs, are obvious.

SUMMARY OF THE INVENTION

The object of the present invention is to propose a device performing a dual function, namely that of detecting the presence of a product in a related seat, as well as the presence of any irregularities in the base section of the product with reference to the base section of a whole product; this all being achieved using a technical solution that is very different from those used until now.

An additional object of the invention consists in proposing a universal device that can, in other words, be used for any shape of product and seat.

A further object of the invention is to propose a device that is reliable, functional and extremely accurate, independent of the material in which the seat for the product and product itself are made.

The above-mentioned objects are obtained using a device for detecting the presence of products in related seats, and any irregularities in the base section of these products when already located in their related seats. The device is mounted on a machine for packaging these products in blister packs. The machine includes motor means for driving a belt; shaping means for producing the said seats in the belt in transverse rows and longitudinal rows which are parallel to the axis of the belt; feed means located downstream of the shaping means in relation to the direction in which the belt is made to advance. The feed means is for placing at least one product in a related seat. The above-mentioned device, located in a check station downstream of the said feed means in relation to the direction in which the belt is made to advance, comprises two operating units, first and second respectively, located on either side of the belt. The first operating unit has a source of electromagnetic radiation located opposite the corresponding face of the belt. This source generates a band of electromagnetic radiation which passes through a strip of the face that is transversely centered in relation to the belt and which extends along an entire transverse row of the seats passing through the check station. The second operating unit has a series of conveying means for the electromagnetic radiation which are laid out in a transverse row that is centered in relation to the strip. There are the same number of these conveying means as there are seats in each transverse row. The inlet section of each conveying means faces the related face of the belt, having a similar section to that of the seats. The inlet section is orientated in exactly the same way as the seats in the related longitudinal row and is centered in relation to this longitudinal row. The inlet section extends by no less than the area delineated by the reference base section of the above-mentioned products. This base section is evaluated in a direction perpendicular to the aforementioned belt. There is at least one receiver for the electromagnetic radiation for each of the aforesaid conveying means. The receiver is located on the outlet section of the related conveying means and supplies an electric output signal that varies in relation to the means intensity of the radiation present in that part of the aforementioned band corresponding to the inlet section of the related conveying means. There is an electric-electronic unit connected to the outputs of the receivers, designed to process the electric signals arriving from the latter in synchronism with the movement of a transverse row of the seats through the check station.

When the product is present, a first electric signal is sent from the output of the receiver mounted on the said conveying means every time each seat is coaxial with the inlet section of the related conveying means, the latter being struck by the "cone of shadow" resultant upon the screening action of the product on the band of radiation.

When the product is missing from the seat in the same conditions as described above, the aforementioned inlet section of the conveying means are struck by the band of radiation, attenuated by the belt alone, and the receiver sends a second electric output signal.

When the base section of the product does not coincide with the reference base section in the condition when the seat and conveying means are coaxial, the intensity of the radiation present in the inlet section of the conveying means falls between the values of the two previous extreme cases, and the receiver generates a third electric output signal.

The device thus checks the area delineated by the base section of the product, independently of the shape of the latter and the material from which it is made; the radiation absorbed by the belt is prevented from influencing the result, by varying the intensity with which the above-mentioned source emits the radiation when setting up the device.

BRIEF DESCRIPTION OF THE DRAWINGS

The characteristics of the invention not have emerged from that stated above, are emphasised hereinafter with specific reference to the enclosed tables of drawings, in which:

FIG. 3 is a diagrammatic illustration of a vertical cross-section of a conveying means-receiver complex whenever a cell with related product is positioned opposite the conveying means;

FIGS. 3a and 3b illustrate cross-sections I—I and II—II in FIG. 3 respectively;

FIG. 4 illustrates the same cross-section as shown in FIG. 3, showing a different embodiment of the conveying means-receiver complex;

DESCRIPTION OF THE PREFERRED EMBODIMENT

Figure 1:
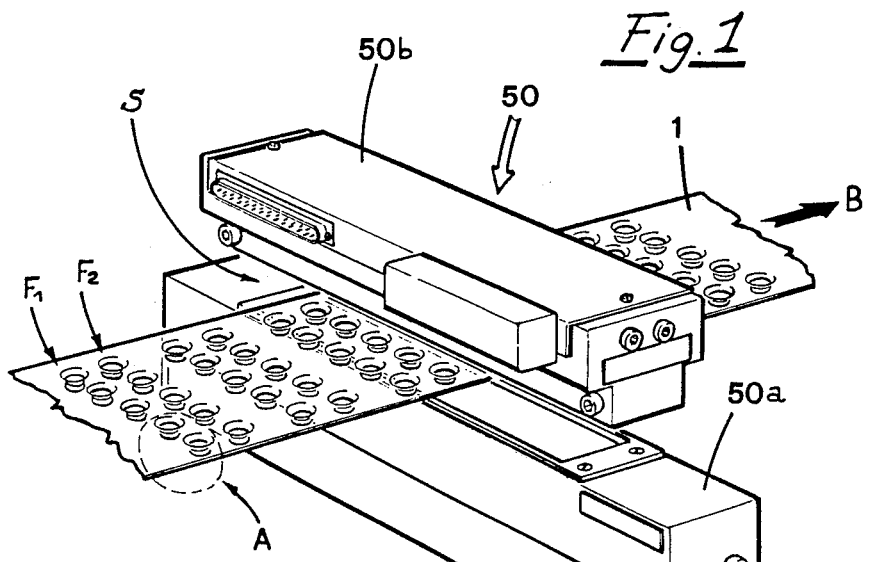
FIG. 1 is a simplified view in perspective of the operating units of which the device is composed, together with the related cellular belt upon which the device itself operates.
Figure 1A:
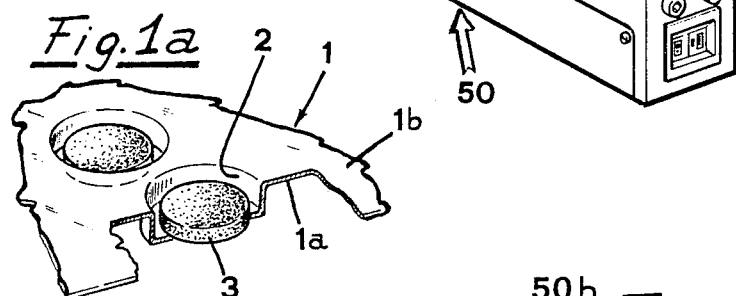
FIG. 1a is a large scale cut-away illustration of detail A in FIG. 1.

With reference to the aforementioned figures, 1 indicates a heat-molded synthetic resin belt in which cells (or seats) 2 have been produced; the cells are all orientated in the same way, forming longitudinal rows F1 that are parallel to the axis of the belt, and transverse rows F2; the cells in every transverse row F2 are equidistant from one another.

Known means, not illustrated, such as continuous operation motor means, for example, drive the belt 1 in direction B parallel to the axis of the belt itself.

Suitable feed means, not illustrated, located in a cell filling station, (also not illustrated), place a related (e.g. pharmaceutical) product 3 in each cell 2.

The device 50 which is the subject of the present invention is located downstream, in relation to direction B, of the cell filling station. The device comprises two operating units 50a, 50b, located on either side of the belt, and together form a check station S through which the belt 1 moves.

The first operating block 50a, positioned below the bottom face 1a of the belt, contains a source 4 (transmitter) of electromagnetic radiation (waves) 5 (e.g. infrared rays), which radiate in a band 6 that strikes against a strip Z of the belt 1 below it, the said strip being tranversely centered in relation to, and at least as long as the belt 1, and being wider than the longitudinal portion occupied by a transverse row F2 of cells 2 (see FIG. 2).

Figure 5:
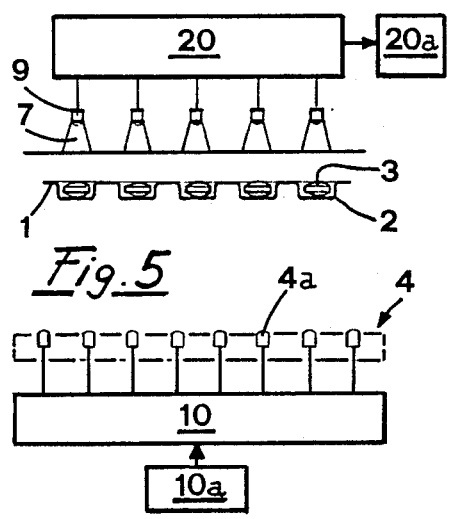
FIG. 5 is a block diagram of the electric-electronic units connected to the device.

In the example illustrated, the source 4 comprises several tranverse rows of emitters 4a (e.g. three rows); the number of these emitters 4a and their position in relation to each other make it possible to obtain a constant intensity for band 6 in the area corresponding to the belt 1. The power supply to the said emitters 4a passes through an adjuster unit 10 (FIG. 5); in this way one can operate on the latter, using, for example, a digital selector, shown by 10a, to vary the intensity of the radiation emitted by each emitter 4a, and thus the intensity of the band in the area corresponding to belt 1. The second operating block 50b contains conveying means 7 for the said radiation 5, which face outwards opposite the top face 1b of the belt 1.

These conveying means have the shape of a truncated cone, with their inlet section 7a facing the belt, and are transversely aligned and equidistant from one another in exactly the same way as the cells 2 in each transverse row F2. In addition to this, each conveying means is symmetrical to the longitudinal plane of symmetry W of a related row F1 of cells.

The inlet section 7a is practically equal to the area delineated by the reference base section 8 of each product 3, that is to say the base section as evaluated in the direction perpendicular to the belt 1 (see FIG. 3a).

The inlet section of each conveying means 7 contains a receiver 9 for the said radiation, e.g.: a phototransistor (FIG. 3), which is struck by the radiation present in the area corresponding to the inlet section 7a of the related conveying means 7; the walls of the latter are specially shaped to convey the aforementioned radiation (by means of the known phenomenon of reflection) directly onto the phototransistor 9.

The outputs of the phototransistors mounted on conveying means 7 are connected to an electronic unit 20 for checking the products and controlling rejects (discussed below), which is not shown in detail, being of known type.

The operation of device 50 will now be described. The belt 1 moves through the check station S, so that each cell 2 moves beneath a related conveying means 7; there is thus an instant in which the cell and conveying means are coaxial.

When this condition is fulfilled, and the product 3 is whole, the conveying means 7 is covered by the "cone of shadow" 11 (FIG. 2) cast by the product 3; in other words, that portion of the above-mentioned band which is directed at the aforementioned conveying means is screened (absorbed) by the product 3, such that only a negligible fraction of that portion reaches the conveying means.

The intensity of radiation present in this fraction varies as a function of the radiation absorbed by the belt (and thus dependent on the thickness of the belt itself, as well as on the material from which it is made), and the intensity with which the radiation is emitted by the emitter 4a; by operating on the selector 10a, when setting up the device, it is possible to adjust the aforesaid intensity so that it results in a corresponding first signal with a voltage V1 (minimum voltage) in the output of the phototransistor 9.

When, in the condition described above, there is no product in the cell, the aforementioned band 6 is present in the inlet section 7a of the conveying means 7, and is thus conveyed by means of the latter on to the phototransistor 9, as a consequence of which the latter generates an outlet signal with a voltage V2 (maximum voltage) that is considerably higher than the value of the previous first signal V1.

The presence or absence of the product in the cell can thus be detected with certainty following the recognition by unit 20 of the respective first and second electric signals V1 and V2.

The device is, furthermore, able to detect whether the product 3 is not whole, (e.g. only a fragment of the latter is present in the cell, or the product has lost parts that crumbled away during handling previous to being placed in the cell, etc.), provided this results in an irregularity (alteration) in the reference base section 8 of the product.

This is illustrated, for example, in product 33, where the base section 88 does not correspond to the reference base section 8 of the remaining products 3 (see FIG. 3a).

As soon as the cell 2 containing the above-mentioned product 33 is coaxial to the related conveying means 7, the "cone of shadow" 111 cast by the aforesaid product 33 forms a faithful image of the base section 88 of the product itself (see FIG. 3b); the inlet section 7a of conveying means is thus struck by an amount of radiation (shown by the broken lines in FIG. 3) that is proportional to the area P, equal to the difference between the reference base section 8 and the base section 88 of the incomplete product 33.

The signal V3 (or third electric signal) generated in the output of the phototransistor 9 is higher than the first signal V1, but lower than the second signal V2; the unit 20 is able to recognize that the third signal V3 differs from the first signal V1 by a preset value which is a percentage of the area P which is missing in relation to the area delineated by the reference base section 8 (e.g. when this value is greater than 15%).

That stated above presupposes that unit 20 analyses (processes) the aforementioned signals V1, V2 and V3 in synchrony with the movement of a transverse row F2 through the check station S, or, to be precise, in exactly the same moment that the cells in this row are coaxial to the conveying means 7; in addition to this, the product must be coaxial to its related cell in order to optimize the above detection operations; this can be satisfied by making the latter in the shape of a truncated cone.

Following on from one another downstream of device 50, there are (as stated in the introduction) suitable means (not illustrated) for applying metal foil by means of heat welding to the top face 1b of the belt, and cutting means (not illustrated) which are operated intermittently to form at least one related blister pack at each operating stroke.

The blister pack for which device 50, by means of phototransistors 9, supplied a first signal VI for every one of its cells 2, is sent to the packaging station referred to in the introduction.

If, on the other hand, the device has sent an electric signal corresponding to either the second signal V2 or third signal V3 for even one single cell 2 to the unit 20, then the unit itself intervenes, activating suitable means 20a, (not shown in detail since not pertinent to the invention), which reject the blister pack being checked.

It is obvious from that stated above that the area covered by the inlet section 7a of each conveying means 7 must not be less than the area delineated by the reference base section 8; were it to be smaller, then any irregularities in the base section falling outside the inlet section 7a would not be detected by the device.

Figure 2:
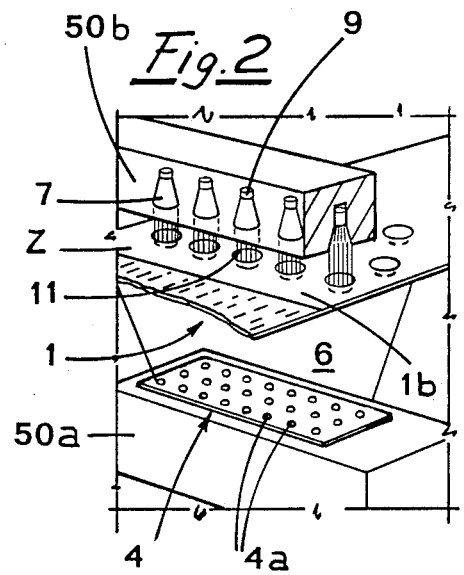
FIG. 2 is a simplified illustration in perspective of the device, showing the most significant aspects of its operation.

FIGS. 1, 2 and 3 concern products with a circumferential reference base section 8.

Two (or more) receivers 9 (FIG. 4) can be fitted to the inlet section 7b of each conveying means for products with an oblong shape (FIG. 4), or for products with a reference base section exceeding a predetermined value.

In the example shown in the enclosed tables, the cells in each row, and the inlet section 7a of the conveying means corresponding to that row are symmetrical in relation to the same longitudinal plane W.

In cases where the cells in each longitudinal row F1 (still orientated, however, in the same way) are not symmetrical in relation to this plane W, (e.g. inclined in relation to the latter), it is necessary for the inlet section 7a to be orientated in exactly the same way as the aforementioned cells, and centred in relation to the related row F1.

The device described above effects an "area check", that is to say it checks the area delineated by the base section of the product, as a consequence having advantages which are comparable to those of known devices using a telecamera; the device is however considerably simpler than the latter, thus having additional advantages with regards to production and running costs.

It is to be understood that the decription supplied herein is purely an unlimited example, and thus that any eventual variations (e.g. the position of the operating units can be changed over, and, furthermore, the shape of the conveying devices may be other than that of a truncated cone), are to be understood as falling within the protective framework afforded to the invention described above and claimed hereinafter.

What is claimed is:

1. A detecting apparatus, comprising:
   a belt having a seat that defines a holding area for holding a product peripherally so that said holding area is completely filled by the product if the product is whole and unbroken;
   means for emitting electromagnetic radiation to pass through said seat; and
   means for receiving any of said radiation that is not shadowed by the product when the product is less than whole in said seat, said receiving means including a receiver defining a receiving area into which said radiation is received, said receiving area being smaller than said holding area so that said receiving area is completely shadowed by the product if the product is whole and unbroken.

2. An apparatus as in claim 1, wherein said receiving means includes a plurality of receivers, said belt including a plurality of seats each defining a holding area for respectively holding products peripherally therein, said belt being movable into a position at which said receivers and said seats are coaxingly aligned with each other.

3. An apparatus as in claim 1, wherein said emitting means includes a plurality of emitters, said receiving means including a plurality of receivers aligned with said emitters respectively.

4. An apparatus as in claim 1, further comprising:
   means for conveying said radiation to said receiver after said radiation passes through said seat and is not completely blocked by the product if the product is less than whole.

5. An apparatus as in claim 4, wherein said conveying means includes a conveyor having a cone shape with an enlarged inlet opening and an outlet opening, said outlet opening being smaller in diameter than said enlarged inlet opening and being closer to said receiver than is said enlarged inlet opening.

6. An apparatus as in claim 4, wherein said belt is movable between said emitting means and said conveyor so that said conveyor has an axis perpendicular to said belt and said conveyor faces and is coaxially aligned with said seat.

7. An apparatus as in claim 4, wherein said receiver produces electrical output signals indicative of said radiation received, further comprising:
   means for processing said electrical signals in synchronism with a movement of said seat between said receiver and said emitting means.

8. An apparatus as in claim 1, wherein said emitting means includes a plurality of emitters of said radiation, said receiving means including a plurality of receivers facing said emitters.

9. A method of detection, comprising the steps of:
   holding a product peripherally in a holding area of a seat in a belt so that the seat is completely filled up by the product if the product is whole and unbroken;
   emitting electromagnetic radiation to pass through said seat; and
   receiving into a receiving area of a receiver any of the radiation that is not shadowed by the product when the product is less than whole and unbroken in the seat, the receiving area being smaller than the holding area of the seat so that the receiving area is completely shadowed by the product if the product is whole and unbroken.

10. A method as in claim 9, further comprising the step of:
    conveying the radiation to the receiver after the radiation passes through the seat and is not completely blocked by the product if the product is less than whole.

11. A method as in claim 10, wherein the step of emitting includes emitting the radiation from an emitter, the step of conveying includes conveying the radiation by a conveyor; further comprising the step of:
    moving the belt between the emitter and the conveyor so that the conveyor has an axis perpendicular to the belt and the conveyor faces and is coaxially aligned with the seat.

12. A method as in claim 10, wherein the step of conveying includes conveying with a cone shaped conveyor.

13. A method as in claim 9, wherein the step of emitting includes emitting the radiation from an emitter, further comprising the steps of:
    producing electrical signals indicative of the received radiation in the receiver; and
    processing the electrical signals in synchronism with a movement of the seat between the receiver and the emitter.

14. A method as in claim 9, wherein the step of receiving includes receiving the radiation in a plurality of receivers, the step of holding including holding a plurality of products in a plurality of holding areas of seats in the belt respectively, further comprising the step of:
    moving the belt into a position in which the plurality of holding areas and receiving areas are coaxially aligned.

15. A method as in claim 14, wherein the step of emitting includes emitting radiation from a plurality of emitters.

16. A method as in claim 14, further comprising the step of:
    conveying the radiation to the receivers through respective conveyors after the radiation passes through the seats.

* * * * *